(12) United States Patent
Tysk et al.

(10) Patent No.: US 9,030,659 B2
(45) Date of Patent: May 12, 2015

(54) SPARK-INDUCED BREAKDOWN SPECTROSCOPY ELECTRODE ASSEMBLY

(71) Applicant: Massachusetts Institute of Technology, Cambridge, MA (US)

(72) Inventors: Shane M. Tysk, Arlington, MA (US); John P. D'Angelo, Medford, MA (US); William D. Herzog, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/948,767

(22) Filed: Jul. 23, 2013

(65) Prior Publication Data

US 2015/0029505 A1    Jan. 29, 2015

(51) Int. Cl.
*G01J 3/30* (2006.01)
*G01N 21/67* (2006.01)

(52) U.S. Cl.
CPC ..................................... *G01N 21/67* (2013.01)

(58) Field of Classification Search
USPC ................................................ 356/300–334
See application file for complete search history.

(56) References Cited

U.S. PATENT DOCUMENTS

| | | | |
|---|---|---|---|
| 2,456,116 A | 12/1948 | Enns | |
| 3,218,514 A | 11/1965 | Bolt | |
| 3,932,785 A | 1/1976 | Suga | |
| 3,940,653 A | 2/1976 | Schnell et al. | |
| 4,009,413 A | 2/1977 | Elliott et al. | |
| 4,046,666 A | 9/1977 | McClanahan et al. | |
| 4,142,127 A | 2/1979 | Suga | |
| 4,496,881 A | 1/1985 | Cheever | |
| 4,789,239 A | 12/1988 | Onishi et al. | |
| 6,034,768 A | 3/2000 | Fraser et al. | |
| 6,265,816 B1 | 7/2001 | Ito et al. | |
| 6,646,365 B1 | 11/2003 | Denissen et al. | |
| 6,963,164 B2 | 11/2005 | Chow et al. | |
| 6,977,469 B2 | 12/2005 | Seinen et al. | |
| 7,701,578 B1 | 4/2010 | Herring | |
| 7,947,965 B2 | 5/2011 | Peters et al. | |
| 8,253,334 B2 | 8/2012 | Jerez | |
| 8,319,410 B2 | 11/2012 | Jerez | |
| 2004/0129449 A1 | 7/2004 | Boettcher et al. | |
| 2004/0223882 A1 | 11/2004 | Bonne et al. | |
| 2008/0068605 A1 | 3/2008 | Herzog et al. | |
| 2013/0148117 A1* | 6/2013 | Kulkarni et al. | 356/313 |

FOREIGN PATENT DOCUMENTS

WO    WO 2013/043600 A1    3/2013

OTHER PUBLICATIONS

Notification of Transmittal of the International Search Report and the Written Opinion of the International Searching Authority, or the Declaration, for International Application No. PCT/US2013/051669, mailed on Jan. 17, 2014 consisting of 16 pages.

* cited by examiner

*Primary Examiner* — Abdullahi Nur
(74) *Attorney, Agent, or Firm* — Hamilton, Brook, Smith & Reynolds, P.C.

(57) ABSTRACT

A spark-induced breakdown spectroscopy apparatus can have a housing with an inlet and an outlet that define an analyte flow path. A laser can define a laser pathway generally transverse to an intersecting the analyte flow path. A pair of electrodes, which can have insulating shields, can be mounted within the housing and can define a spark path. An optical detection element defines an optical path. The apparatus can be used to identify an aerosolized analyte.

47 Claims, 6 Drawing Sheets

SPARK-INDUCED BREAKDOWN SPECTROSCOPY ELECTRODE ASSEMBLY

GOVERNMENT SUPPORT

This invention was made with government support under USAF FA8721-05-C-0002 from the United States Department of Defense. The government has certain rights in the invention.

BACKGROUND OF THE INVENTION

Spark-induced breakdown spectroscopy ("SIBS") is an atomic emission spectroscopic technique that can be used to detect and quantify the elemental content of an analyte. In operation, a powerful electric spark discharge between two electrodes creates a small volume of a high-temperature plasma. An analyte, which may be aerosolized, is quickly vaporized and/or atomized by the plasma. High-energy electrons from the electric spark excite the analyte atoms to one or more excited electronic states. As an element relaxes back toward the ground state, it emits a characteristic atomic emission spectrum which is detected by a spectrometer and recorded. Based on the signature emission spectrum, the elemental content of the analyte can be determined. A representative SIBS apparatus is disclosed in U.S. Pat. No. 6,034,768, the entire teachings of which are incorporated herein by reference.

Such systems can be used for real-time detection of elements in an analyte, which may be used to detect the presence of hazardous airborne heavy metals, such as lead or chromium, or other chemicals, such as chemical or biological weapons. Other applications of the technology include process control, emission compliance, and industrial hygiene.

While SIBS is a sensitive technique for elemental detection, it is not without its drawbacks. Generating a spark requires the use of two electrodes positioned at an appropriate distance. Over time, the electrodes wear down and become smaller in length, which causes two problems. As the electrodes degrade, debris from the electrodes accumulates within the housing where the spark is generated. This debris can coat the optical equipment and reduce sensitivity of the apparatus, thereby requiring periodic cleaning. In addition, as the electrodes erode, the location of the spark may shift. In precision analytical equipment, even modest adjustments in the location of the spark can impact the sensitivity of the measurement.

Accordingly, there is a need for an improved SIBS apparatus that can be used to determine the elemental content of an analyte, particularly an aerosolized analyte, that substantially prevents debris from fouling the optical equipment and at least partially stabilizes the spark location.

SUMMARY OF THE INVENTION

A spark-induced breakdown spectroscopy (SIBS) apparatus of the invention includes a housing having an inlet and an outlet that define an analyte flow path from the inlet to the outlet of the housing. A laser defines a laser pathway generally transverse to and intersecting the analyte flow path. A pair of electrode mounts are arranged within the housing such that tips of electrodes mounted in the housing define a line that is generally transverse to the analyte flow path. An insulating shield is at each electrode mount. The edges of the insulating shields at least partially define a spark path that is transverse to and intersecting at a point in the analyte flow path and downstream along the analyte flow path from the point of intersection of the laser pathway and the analyte flow path. An optical detection element defines an optical path generally transverse to the analyte flow path at a point proximate to the intersection of the spark path and the analyte flow path. The tips of the electrodes and insulating shields can be generally parallel to the laser pathway. The optical pathway can be generally transverse to the spark path. Electrodes can be mounted on the electrode mounts, and the shields can be sleeves that at least partially surround the electrode and extend beyond the tip of the electrode. The SIBS apparatus can also include an advancement component at each of the electrodes, whereby each electrode can advance along its respective major longitudinal axis as each electrode erodes at its respective tip to thereby keep each tip essentially in the same position within the chamber, whereby the path of the spark defined by the tips and insulating shields is maintained at an essentially constant length. The distal end of the sleeves can have an opening that is located beyond the tip of its respective electrode. The opening can have a diameter that is essentially that of the diameter of the electrode, or the opening can be smaller than that of the electrode. The openings can be coplanar with a plane extending transversely to the major axis of the electrode, at portions of the sleeves that are most proximal to each other, at portions of the sleeves most distal from each other, at portions of the sleeves intermediate between the most proximal and most distal positions, or coplanar with a plane having an axis parallel to a major longitudinal axis of the respective electrode. The major longitudinal axes of the electrodes can be collinear, can intersect at a positive angle in the plane of the path of the analyte through the chamber, can intersect at an angle of about 90 degrees, or can be essentially parallel. The electrodes have a diameter in a range of between about 0.25 mm and about 5 mm. The electrodes can include at least one member of the group consisting of rhenium, silver, molybdenum, tungsten, or iridium. The insulating shields can be made of alumina, polytetrafluoroethylene, glass, and various plastics. The SIBS apparatus can further include a focusing mirror within the housing positioned to reflect light towards the optical detection element. The SIBS apparatus can further include a lens within the housing positioned to focus light toward the optical detection element. The optical detection element can be an optically dispersive spectrometer with a focal plane that records an optical spectrum, or can be one or more detectors, such as photomultiplier tubes or photodiodes, with narrow bandpass optical filters. The tips of the electrodes and insulating shields can be generally parallel to the laser pathway. The optical path can be generally transverse to the spark pathway.

A method for conducting spark-induced breakdown spectroscopy includes directing an analyte through a housing as an aerosol. The housing has an inlet and an outlet defining an analyte flow path from the inlet to the outlet of the housing. A laser is directed generally transverse to and intersecting the analyte flow path. A spark is generated across the analyte flow path between a pair of electrodes mounted within the housing. Each electrode has a tip, wherein a straight line extending between the tips of the electrodes is traversed by shields, a shield being mounted at each electrode, and wherein the shields each have an edge, the edges at least partially defining a spark path that is generally transverse to and intersecting at a point in the analyte flow path and downstream along the analyte flow path from the point of intersection of the laser pathway and the analyte flow path such that a spark ionizes the analyte to form a plasma. An emission is received from the ionized analyte by an optical detection element in order to optically identify the analyte following ionization as it continues along its path through the housing. The shields can each be a sleeve that at least partially surrounds the electrode and extends beyond the tip of each electrode. The method can further include an advancement component at each of the electrodes, whereby each electrode is advanced along its respective major longitudinal axis as each electrode erodes at its respective tip to thereby keep each tip essentially in the same position within the chamber, whereby the path of the spark defined by the tips and insulating shield is maintained at an essentially constant length. The sleeves can each define an opening at an end of the sleeve that is located beyond the tip of its respective electrode, and wherein the edge is defined by the opening. The opening can have a diameter that is essentially that of the diameter of the electrode, or the opening can be smaller than that of the electrode. The openings can be coplanar with a plane extending transversely to the major axis of its respective electrode, at portions of the sleeves that are most proximal to each other, at portions of the sleeves most distal from each other, or coplanar with a plane having an axis parallel to a major longitudinal axis of the respective electrode. The major longitudinal axes of the electrodes can be collinear, intersect at a positive angle in the plane of the path of the analyte through the chamber, intersect at an angle of about 90 degrees, or be essentially parallel. The electrodes can have a diameter in a range of between about 0.25 mm and about 5 mm. The electrodes can include at least one member of the group consisting of rhenium, silver, molybdenum, tungsten, or iridium. The insulating shields can be made of alumina, polytetrafluoroethylene, glass, and various plastics. At least a part of the emission from the ionized analyte can be reflected towards the optical detection element by a focusing mirror within the housing. At least a part of the emission from the ionized analyte can be focused towards the optical detection element by a lens within the housing. The optical detection element can be an optically dispersive spectrometer with a focal plane that records an optical spectrum, or can be one or more detectors, such as photomultiplier tubes or photodiodes, with narrow bandpass optical filters. The tips of the electrodes and insulating shields can be generally parallel to the laser pathway. The optical path can be generally transverse to the spark pathway.

A spark-generating device can have a pair of electrodes, each having a tip. The two tips define a spark path. An insulating shield is proximal to each tip and in an interfering relation with the spark path such that each shield defines a opening through which the spark passes.

The improved SIBS apparatus disclosed herein has several advantages. The insulating sleeves can control the debris emitted from the electrode. In operation, the debris can coat the optics of the SIBS apparatus. When the optics are coated, the SIBS apparatus must be cleaned, which not only requires additional labor, but results in downtime of the SIBS apparatus. Thus, controlling the debris from the electrode reduces maintenance costs and increases operational time. Additionally, the insulating sleeves can control the spark localization, even as the electrodes erode during use. Since the spark generates the plasma, controlling the spark location is important to improve sensitivity of the SIBS apparatus, particularly when the analyte has been aerosolized.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A is a front view of a cross section of a schematic representation of an SIBS apparatus of one embodiment of the invention.

FIG. 1B is a plan view of a cross section of a schematic representation of an SIBS apparatus of one embodiment of the invention.

FIG. 1C is a side view of a cross section of a schematic representation of an SIBS apparatus of one embodiment of the invention.

FIG. 2 is a view, partly in cross-section, of a pair of electrode mounts of the prior art.

FIG. 3 is a view, partly in cross-section, of a pair of electrode mounts of one embodiment of the invention having insulating sleeves and open ends.

FIG. 4 is a view, partly in cross-section, of a pair of electrode mounts of the embodiment of the invention of FIG. 3 having insulating sleeves, open ends, and eroded electrodes.

FIG. 5 is a view, partly in cross-section, of a pair of electrode mounts of another embodiment of the invention having insulating sleeves with an opening on the distal surface that is smaller than the diameter of the electrode.

FIG. 6 is a view, partly in cross-section, of a pair of electrode mounts of still another embodiment of the invention having insulating sleeves with an opening on the distal surface that is offset from the center.

FIG. 7A is a view, partly in cross-section, of a pair of electrode mounts of yet another embodiment of the invention having insulating sleeves with an opening on the surface of the sheath, wherein the major longitudinal axes of the electrode mounts intersect at an angle of about 90°.

FIG. 7B is a view, partly in cross-section, of a pair of electrode mounts of an embodiment of the invention having insulating sleeves with an opening on the surface of the sheath, wherein the major longitudinal axes of the electrode mounts are essentially parallel.

FIG. 7C is a view, partly in cross-section, of a pair of electrode mounts of an embodiment of the invention having insulating sleeves with an opening on the distal surface of the sheath, wherein the major longitudinal axes of the electrode mounts are collinear.

FIG. 8 is a view, partly in cross-section, representative of one embodiment of the invention having an electrode mount that includes a spring-loaded mechanism for advancing the mounted electrode.

FIG. 9 is a schematic representation of another embodiment of the invention.

DETAILED DESCRIPTION OF THE INVENTION

FIGS. 1A, 1B, and 1C illustrate an exemplary SIBS apparatus 100 of the invention. As shown, SIBS apparatus 100 includes housing 105 having inlet 110 and outlet 115. An analyte enters housing 105 at inlet 110, flows along analyte flow path 120, and exits housing 105 at outlet 115. The housing 105 can be any suitable material for use in spark-induced breakdown spectroscopy (SIBS), typically those that can shield from electromagnetic radiation, such as nickel-coated aluminum, stainless steel, polytetrafluoroethylene, ceramic, or other metals.

A laser 280 defines a laser pathway 289 by providing light through windows 283 on either side of the housing. The laser pathway 289 is generally transverse to and intersects the analyte flow path 120.

A pair of electrode mounts 200 are contained within housing 105 such that tips of electrodes 220 are positioned at the ends of a line that is generally transverse to the analyte flow path 120 and generally parallel to the laser pathway 289. The electrodes can have any suitable diameter for generating a spark, typically ranging from about 0.25 mm to about 5 mm. The electrodes can be made from any suitable material, such as rhenium, silver, molybdenum, tungsten, or iridium. One of skill in the art will understand that the electrode can be made of many other materials, as may be suitable to optimize detection of an analyte or components of an analyte.

Insulating shield 270 at least partially surrounds electrode 220. At a minimum, the shield 270 has a higher dielectric constant than air. Preferably, the shield 270 has minimal spectral lines or a complete absence of spectral lines. Suitable materials of construction of shield 270 include, for example, alumina, polytetrafluoroethylene, glass, and various plastics. One of skill in the art will recognize that the shield can be made of many other types of material, so long as it is sufficiently insulating to cause a spark typically used in SIBS to be diverted about insulating shield 270. Each shield 270 has an edge 275, and the combination of edges 275 and tips of the electrodes 220 defines a spark path 250 for a spark generated between electrodes 220. Spark path 250 is transverse to and in the analyte flow path 120, generally parallel to the laser pathway 289, and downstream along the analyte flow path 120 relative to the laser pathway 289. Thus, spark 250 generated between the tips of electrodes 220 will extend across edges 275 of shields 270 and across analyte flow path 120 and intersect the optical detection path 130.

Optical detection element 125 defines optical path 130 generally transverse to the analyte flow path. Examples of optical detection elements 125 suitable for use in the spark-induced breakdown spectroscopy analysis apparatus of the invention are known in the art and include, for example, an optically dispersive spectrometer with a focal plane that records an optical spectrum, or can be one or more detectors, such as photomultiplier tubes or photodiodes, with narrow bandpass optical filters. An optional focusing mirror 293 within the housing 105 can be positioned to reflect light towards the optical detection element 125. An optional lens 298 can be positioned within the housing 105 to focus light toward the optical detection element 125.

Figure 1A:
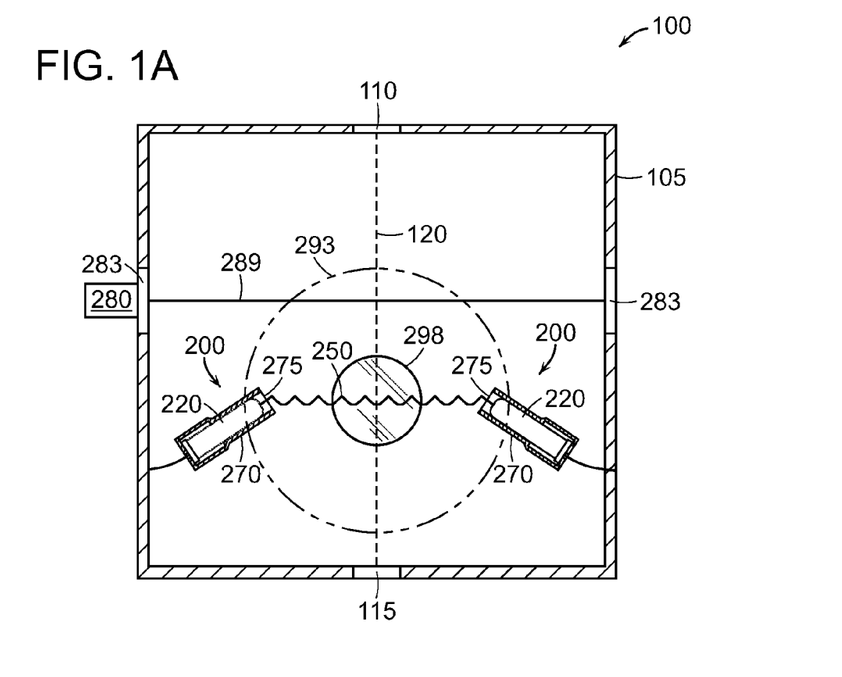
Figure 1B:
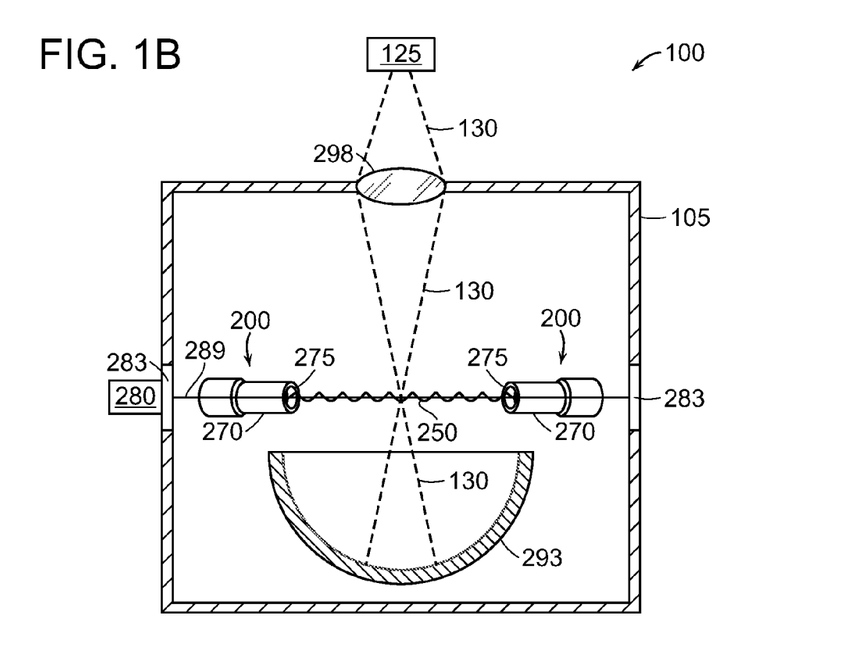
Figure 1C:
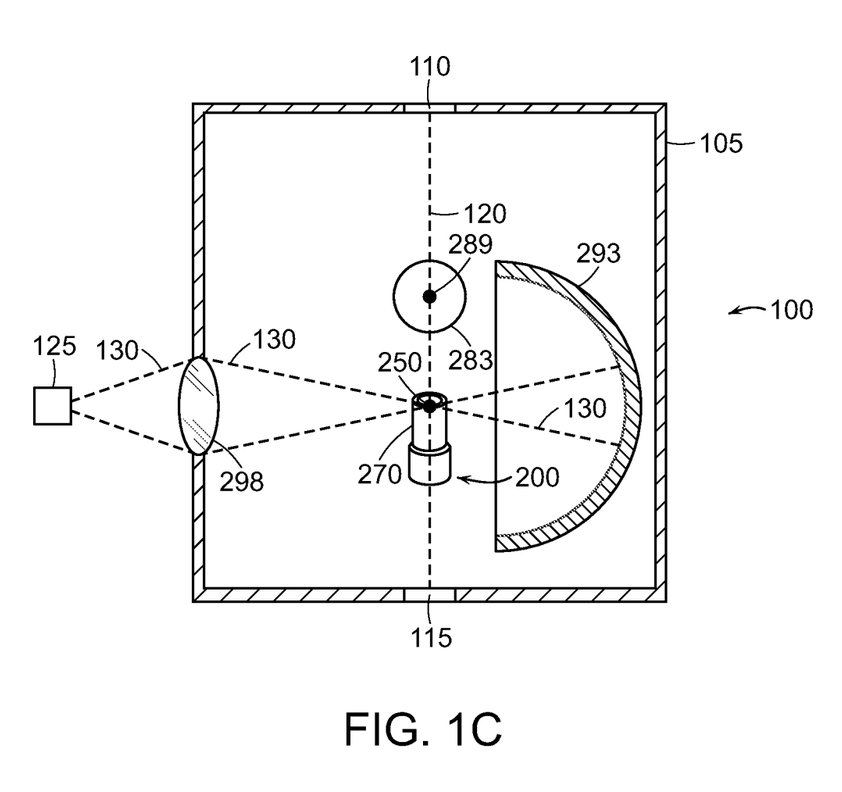
Figure 2:
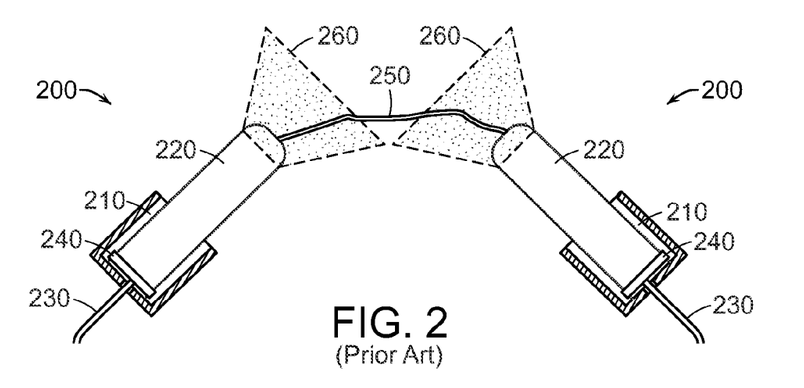

FIG. 2 illustrates a prior art electrode mount 200. Electrode mount 200 includes holder 210 that is adapted to secure electrode 220. Electrode 220 is electrically coupled to the SIBS apparatus via electrical conductor 230 and contacting portion 240. Electrical spark 250 is generated between electrodes 220. As FIG. 2 illustrates, each electrode 220 extends beyond its holder 210. In the prior art electrode mount 200, the zone 260 of ablation of particles from electrode 220 is widespread.

Figure 3:
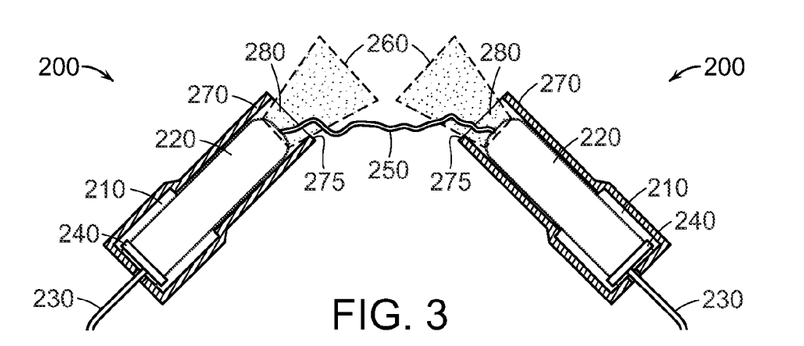

FIG. 3 is a view, shown partly in cross-section, of one embodiment of a pair of electrode mounts as arranged in an SIBS apparatus of the invention, having an insulating sleeve 270 that at least partially surrounds the electrode 220. Insulating sleeve 270 defines open end 280. Open end 280 defines edge 275 that traverses a straight line between electrodes 220. As compared to the prior art electrode mount (FIG. 2), the location of the spark 250 is defined, at least in part, by edges 275 because the spark 250 must circumvent edges 275. Additionally, because each spark 250 causes a small amount of ablation of material from surfaces of electrodes 220, the zone 260 of material ablated from electrodes 220 is at least partially limited by insulating sleeves 270, thereby partially reducing fouling of other parts of SIBS apparatus 100, such as windows 283, focusing mirror 293, and lens 298.

Figure 4:
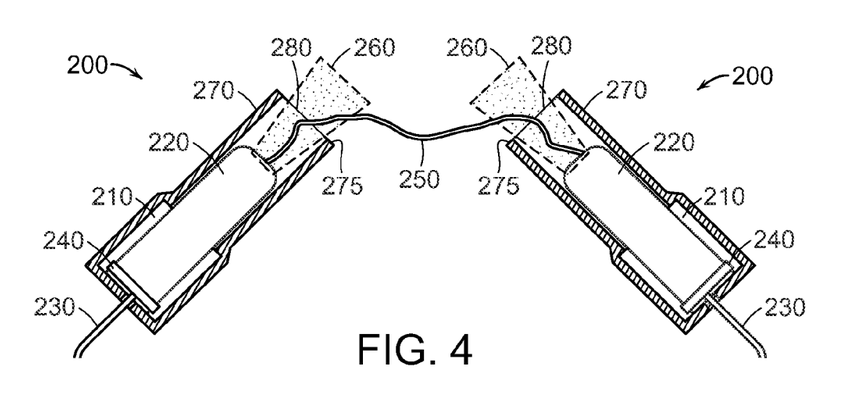

FIG. 4 is a view of the embodiment shown in FIG. 3, whereby electrodes 220 are eroded, yet the position of spark path 250 remains relatively constant, as defined, at least in part, by edges 275, relative to the prior art electrode of FIG. 2.

Figure 5:
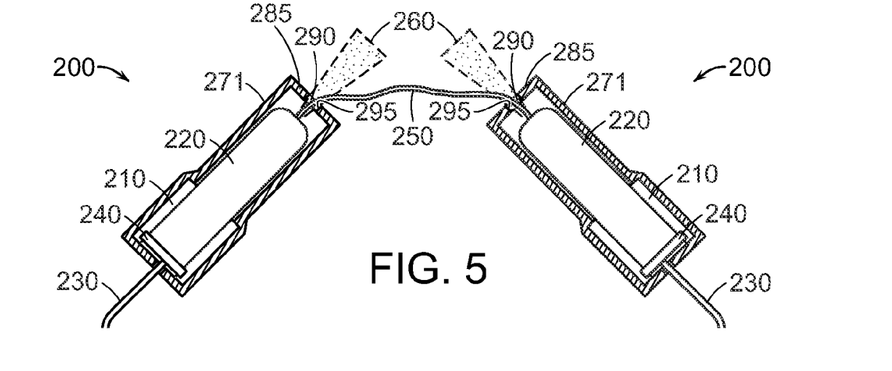

FIG. 5 is a view of a pair of electrode mounts of one embodiment of the invention having insulating sleeve 271 that defines opening 290 on distal surface 285 that is smaller than the diameter of the electrode 220. As shown in FIG. 5, the smaller openings 290 defines edges 295 that further restrict the position of the spark 250 and confines the zone 260 of ablation of particles from electrode 220. Opening 290 is located approximately in the center of distal surface 285.

Figure 6:
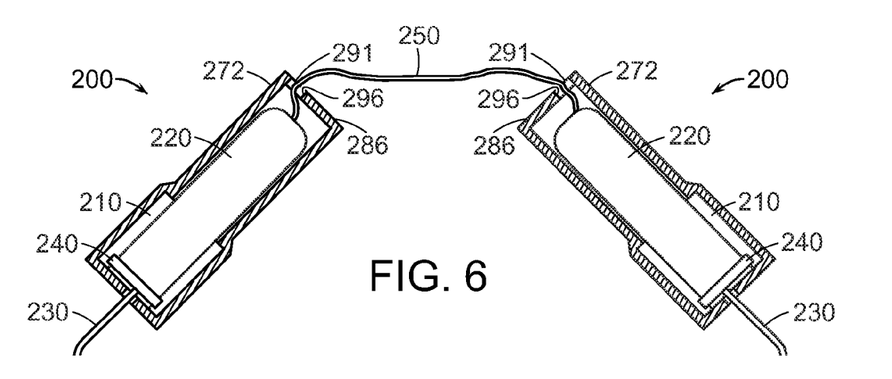

FIG. 6 is a view of a pair of electrode mounts of another embodiment of the invention having insulating sleeve 272 that defines opening 291 on distal surface 286 that is smaller than the diameter of electrode 220. Openings 291 define edges 296 and are positioned on distal surface 286 of each sleeve 272 such that openings 291 are most distal from each other. Although not shown, openings 291 can be positioned on distal surface 286 of each sleeve 272 such that the openings are most proximal to each other.

Figure 7A:
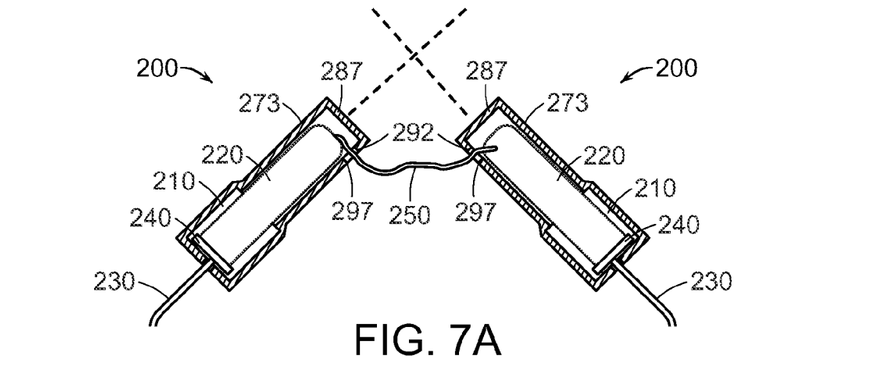
Figure 7B:
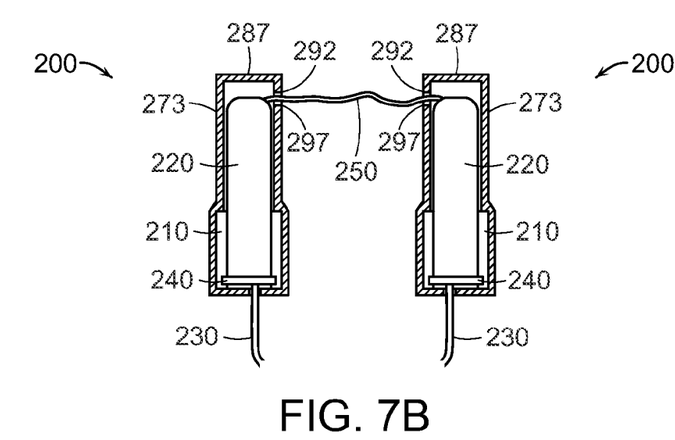
Figure 7C:
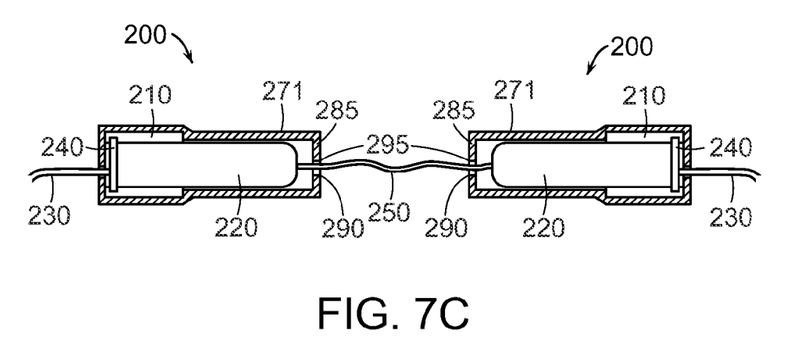

FIGS. 7A-7C illustrate spatial arrangements of the electrode mounts of yet another embodiment of the invention defining an alternative location of opening 292 that defines edges 297. As illustrated in FIGS. 7A and 7B, opening 292 can be located on sleeve 273 such that distal end 287 is fully closed. Openings 292 in FIGS. 7A and 7B are located at portions of the sleeves most proximal to each other. FIG. 7A illustrates a pair of electrode mounts, wherein the major longitudinal axes of the electrode mounts intersect at an angle of about 90°. One particular advantage of the arrangement of FIG. 7A is that ablated debris from the electrode falls downward and minimizes interference with optics of the SIBS apparatus. FIG. 7B illustrates yet another arrangement of a pair of electrode mounts suitable for use with the invention, wherein the major longitudinal axes of the electrode mounts are essentially parallel. FIG. 7C illustrates a pair of electrode mounts suitable for use with the invention, wherein the major longitudinal axes of the electrode mounts are collinear.

Figure 8:
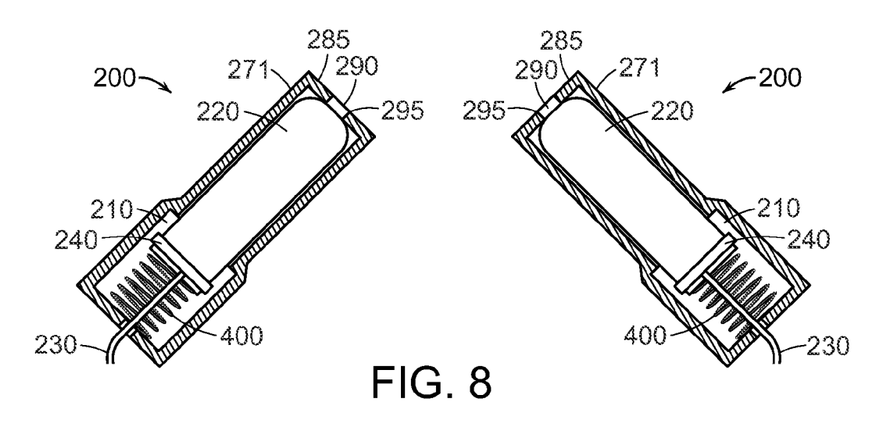

FIG. 8 is a view, partly in cross-section, representative of another embodiment of the invention having an electrode mount that includes spring-loaded mechanism 400 for advancing the mounted electrode. Spring-loaded mechanism 400 advances each electrode 220 along its respective major longitudinal axis as each electrode 220 erodes at its respective tip to thereby keep each tip essentially in the same position within the housing. Thus, the spark path 250 (not shown in FIG. 8) is maintained at an essentially constant length.

Figure 9:
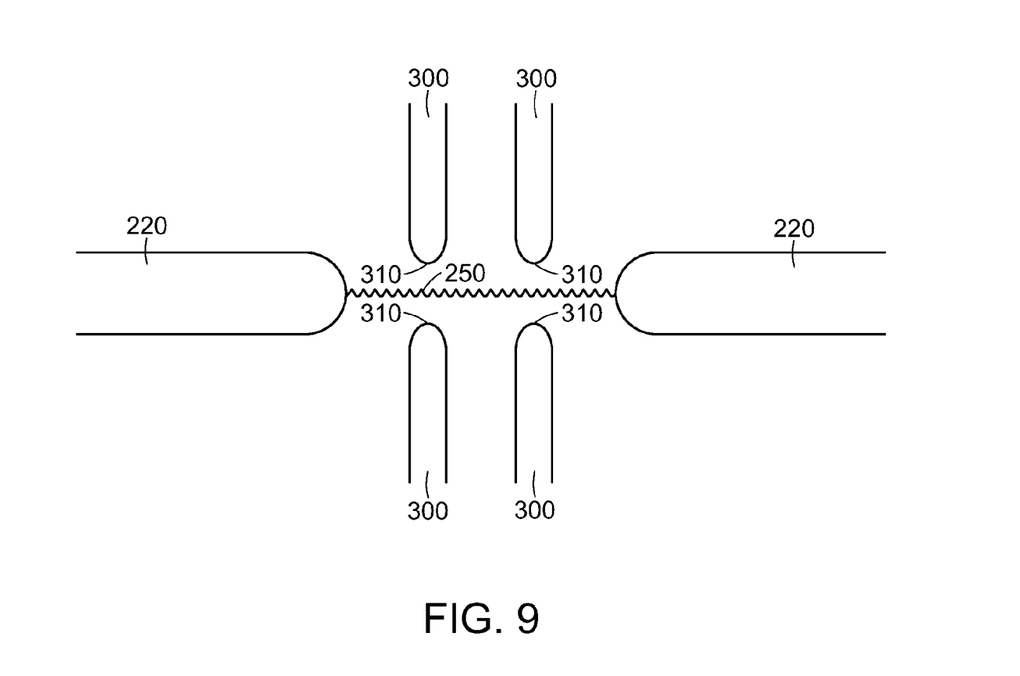

FIG. 9 is a spark-generating device of the invention. The spark-generating device has a pair of electrodes 220. The tips of the two electrodes define spark path 250. One or more insulating shields 300 define edges 310 and are positioned in an interfering relation with the spark path such that edges define, at least in part, spark path 250. In one embodiment, the shield 300 can be a hollow cylinder.

In operation, an analyte, which can be aerosolized, flows from inlet 110 to outlet 115 along analyte flow path 120. The analyte crosses the laser pathway 289. The laser can be used to measure the size and fluorescence of the analyte to thereby detect whether a particle of interest has crossed the laser pathway. If the particle is a particle of interest, a spark can be generated along spark path 250, thereby creating a cloud of ionized plasma for approximately one half of a microsecond. The ionized cloud of plasma then emits a spectrum characteristic of the analyte, which is detected by the optical detection element 125.

EQUIVALENTS

While this invention has been particularly shown and described with reference to example embodiments thereof, it will be understood by those skilled in the art that various changes in form and details may be made therein without departing from the scope of the invention encompassed by the appended claims.

What is claimed is:

1. A spark-induced breakdown spectroscopy apparatus, comprising:
    a) a housing having an inlet and an outlet defining an analyte flow path from the inlet to the outlet of the housing;
    b) a laser defining a laser pathway generally transverse to and intersecting the analyte flow path;
    c) a pair of electrode mounts within the housing, whereby tips of electrodes mounted in the housing define a line that is generally transverse to the analyte flow path;
    d) an insulating shield at each electrode mount, the insulating shields each having an edge, wherein the edges at least partially define a spark path that is transverse to and intersecting at a point in the analyte flow path and downstream along the analyte flow path from the point of intersection of the laser pathway and the analyte flow path, wherein the shields are each a sleeve that at least partially surrounds the electrode and extends beyond the tip of each electrode, and wherein the sleeves each define an opening at an end of the sleeve that is located beyond the tip of its respective electrode; and
    e) an optical detection element defining an optical path generally transverse to the analyte flow path and intersecting the analyte flow path at a point proximate to the intersection of the spark path and the analyte flow path.

2. The spark-induced breakdown spectroscopy apparatus of claim 1, further including electrodes mounted in the electrode mounts.

3. The spark-induced breakdown spectroscopy apparatus of claim 1, further including an advancement component at each of the electrodes, whereby each electrode can be advanced along its respective major longitudinal axis as each electrode erodes at its respective tip to thereby keep each tip essentially in the same position within the housing, whereby the path of the spark defined by the tips and insulating shield is maintained at an essentially constant length.

4. The spark-induced breakdown spectroscopy apparatus of claim 1, wherein the opening has a diameter that is essentially that of the diameter of the electrode.

5. The spark-induced breakdown spectroscopy apparatus of claim 1, wherein the diameter of the opening is smaller than that of the electrode.

6. The spark-induced breakdown spectroscopy apparatus of claim 1, wherein the openings are coplanar with a plane extending transversely to the major axis of its respective electrode.

7. The spark-induced breakdown spectroscopy apparatus of claim 1, wherein the openings are at portions of the sleeves that are most proximal to each other.

8. The spark-induced breakdown spectroscopy apparatus of claim 1, wherein the openings are at portions of the sleeves most distal from each other.

9. The spark-induced breakdown spectroscopy apparatus of claim 1, wherein the openings are at portions of the sleeves intermediate between portions of the sleeves that are most proximal and most distal from each other.

10. The spark-induced breakdown spectroscopy apparatus of claim 1, wherein the openings are coplanar with a plane having an axis parallel to a major longitudinal axis of the respective electrode.

11. The spark-induced breakdown spectroscopy apparatus of claim 1, wherein the major longitudinal axes of the electrodes are collinear.

12. The spark-induced breakdown spectroscopy apparatus of claim 1, wherein the major longitudinal axes of the electrodes intersect at a positive angle in the plane of the path of the analyte through the housing.

13. The spark-induced breakdown spectroscopy apparatus of claim 1, wherein the major longitudinal axes of the electrodes intersect at an angle of about 90 degrees.

14. The spark-induced breakdown spectroscopy apparatus of claim 1, wherein the major longitudinal axes of the electrodes are essentially parallel.

15. The spark-induced breakdown spectroscopy apparatus of claim 1, wherein the electrodes have a diameter in a range of between about 0.25 mm and about 5 mm.

16. The spark-induced breakdown spectroscopy apparatus of claim 1, wherein the electrodes include at least one member of the group consisting of rhenium, silver, molybdenum, tungsten, and iridium.

17. The spark-induced breakdown spectroscopy apparatus of claim 1, wherein the insulating shields include at least one member selected form the group consisting of alumina, polytetrafluoroethylene, glass, and plastic.

18. The spark-induced breakdown spectroscopy apparatus of claim 1, further comprising a focusing mirror within the housing positioned to reflect light towards the optical detection element.

19. The spark-induced breakdown spectroscopy apparatus of claim 1, further comprising a lens within the housing positioned to focuses light toward the optical detection element.

20. The spark-induced breakdown spectroscopy apparatus of claim 1, wherein the optical detection element is an optically dispersive spectrometer with a focal plane that records an optical spectrum.

21. The spark-induced breakdown spectroscopy apparatus of claim 1, wherein the optical detection element is one or more photomultiplier tubes or photodiodes.

22. The spark-induced breakdown spectroscopy apparatus of claim 21, wherein the one or more photomultiplier tubes or photodiodes further includes a narrow bandpass optical filter.

23. The spark-induced breakdown spectroscopy apparatus of claim 1, wherein the tips of the electrodes and insulating shields are generally parallel to the laser pathway.

24. The spark-induced breakdown spectroscopy apparatus of claim 1, wherein the optical path is generally transverse to the spark path.

25. A method for conducting spark-induced breakdown spectroscopy, comprising the steps of:
    a) directing an analyte through a housing as an aerosol particle, wherein the housing has an inlet and an outlet defining an analyte flow path from the inlet to the outlet of the housing;
    b) directing a laser along a laser pathway generally transverse to and intersecting the analyte flow path;
    c) generating a spark across the analyte flow path between a pair of electrodes mounted within the housing, each electrode including a tip, a straight line extending between the tips of the electrodes being traversed by shields, a shield being mounted at each electrode, and wherein the shields each have an edge, the edges at least partially defining a spark path that is generally transverse to and intersecting at a point in the analyte flow path and downstream along the analyte flow path from the point of intersection of the laser pathway and the analyte flow path, wherein the shields are each a sleeve that at least partially surrounds the electrode and extends beyond the tip of each electrode, and wherein the sleeves each define an opening at an end of the sleeve that is located beyond the tip of its respective electrode, and wherein the edge is defined by the opening, whereby the spark ionizes the analyte to form a plasma; and d) receiving an emission from the ionized analyte by an optical detection element along an optical pathway to optically identify the analyte following ionization as it continues along its path through the housing.

26. The method for conducting spark-induced breakdown spectroscopy of claim 25, further including an advancement component at each of the electrodes, whereby each electrode can be advanced along its respective major longitudinal axis as each electrode erodes at its respective tip to thereby keep each tip essentially in the same position within the housing, whereby the path of the spark defined by the tips and insulating shield is maintained at an essentially constant length.

27. The method for conducting spark-induced breakdown spectroscopy of claim 25, wherein the opening has a diameter that is essentially that of the diameter of the electrode.

28. The method for conducting spark-induced breakdown spectroscopy of claim 25, wherein the diameter of the opening is smaller than that of the electrode.

29. The method for conducting spark-induced breakdown spectroscopy of claim 25, wherein the openings are coplanar with a plane extending transversely to the major axis of its respective electrode.

30. The method for conducting spark-induced breakdown spectroscopy of claim 25, wherein the openings are at portions of the sleeves that are most proximal to each other.

31. The method for conducting spark-induced breakdown spectroscopy of claim 25, wherein the openings are at portions of the sleeves most distal from each other.

32. The method for conducting spark-induced breakdown spectroscopy of claim 25, wherein the openings are coplanar with a plane having an axis parallel to a major longitudinal axis of the respective electrode.

33. The method for conducting spark-induced breakdown spectroscopy of claim 25, wherein the major longitudinal axes of the electrodes are collinear.

34. The method for conducting spark-induced breakdown spectroscopy of claim 25, wherein the major longitudinal axes of the electrodes intersect at a positive angle in the plane of the path of the analyte through the housing.

35. The method for conducting spark-induced breakdown spectroscopy of claim 25, wherein the major longitudinal axes of the electrodes intersect at an angle of about 90 degrees.

36. The method for conducting spark-induced breakdown spectroscopy of claim 25, wherein the major longitudinal axes of the electrodes are essentially parallel.

37. The method for conducting spark-induced breakdown spectroscopy of claim 25, wherein the electrodes have a diameter in a range of between about 0.25 mm and about 5 mm.

38. The method for conducting spark-induced breakdown spectroscopy of claim 25, wherein the electrodes include at least one member of the group consisting of rhenium, silver, molybdenum, tungsten, and iridium.

39. The method for conducting spark-induced breakdown spectroscopy of claim 25, wherein the insulating shields include at least one member selected form the group consisting of alumina, polytetrafluoroethylene, glass, and plastic.

40. The method for conducting spark-induced breakdown spectroscopy of claim 25, wherein at least part of the emission from the ionized analyte is reflected towards the optical detection element by a focusing mirror within the housing.

41. The method for conducting spark-induced breakdown spectroscopy of claim 25, wherein at least part of the emission from the ionized analyte is focused towards the optical detection element by a lens within the housing.

42. The method for conducting spark-induced breakdown spectroscopy of claim 25, wherein the optical detection element is an optically dispersive spectrometer with a focal plane that records an optical spectrum.

43. The method for conducting spark-induced breakdown spectroscopy of claim 25, wherein the optical detection element is one or more photomultiplier tubes or photodiodes.

44. The method for conducting spark-induced breakdown spectroscopy of claim 43, wherein the one or more photomultiplier tubes or photodiodes further includes a narrow bandpass optical filter.

45. The method for conducting spark-induced breakdown spectroscopy of claim 25, wherein the tips of the electrodes and insulating shields are generally parallel to the laser pathway.

46. The method for conducting spark-induced breakdown spectroscopy of claim 25, wherein the optical pathway is generally transverse to the spark path.

47. The method for conducting spark-induced breakdown spectroscopy of claim 25, wherein the openings are at portions of the sleeves intermediate between portions of the sleeves that are most proximal and most distal from each other.

* * * * *